US00PP15211P2

(12) United States Plant Patent
White

(10) Patent No.: US PP15,211 P2
(45) Date of Patent: Oct. 12, 2004

(54) ***CLEMATIS* PLANT NAMED 'WHITE ABUNDANCE'**

(50) Latin Name: *Clematis cartmanii*
Varietal Denomination: White Abundance

(76) Inventor: Anthony Robin White, Alresford, Hampshire (GB)

( * ) Notice: Subject to any disclaimer, the term of this patent is extended or adjusted under 35 U.S.C. 154(b) by 208 days.

(21) Appl. No.: 10/241,540

(22) Filed: Sep. 11, 2002

(51) Int. Cl.[7] ..... A01H 5/00
(52) U.S. Cl. ..... Plt./228
(58) Field of Search ..... Plt./228

*Primary Examiner*—Bruce R. Campell
*Assistant Examiner*—Michelle Kizilkaya

(57) ABSTRACT

A new cultivar of *Clematis* named 'White Abundance' that is characterized by short internodes, green fern-like foliage and a profuse display of fragrant cream-white male flowers in spring. In combination these traits set 'White Abundance' apart from all other existing varieties of *Clematis* known to the inventor.

2 Drawing Sheets

Genus: *Clematis*.
Species: *cartmanii*.
Denomination: White Abundance.

BACKGROUND OF THE INVENTION

The present invention relates to a new and distinct cultivar of *Clematis* that is grown for use as a sub-shrub in the landscape. The new cultivar is known botanically as a *Clematis*×*cartmanii* and will be referred to hereinafter by the cultivar name 'White Abundance'.

'White Abundance' resulted from a formal breeding program. The inventor bred 'White Abundance' in 1994 by induced hybridization between the pollen parent *Clematis* 'Avalanche' (unpatented) and the seed parent *Clematis* 'White Cascade' (unpatented). The cross was conducted in a cultivated area of Hampshire, England and 'White Abundance' was selected based on the unique and distinguishing traits of foliage form and color as well as short internodes. 'White Abundance' is a hybrid exhibiting panicles of fragrant cream-white flowers bloom in spring.

The closest comparison plant is *Clematis*×*cartmanii* 'Joe' (unpatented). 'White abundance' is distinguishable from the comparison plant by short internodes and the form and color of the foliage. At maturity 'White Abundance' is 0.75–1.25 meters in height and 0.75–1.25 meters in width. 'White Abundance' differs from the parent plants 'Avalanche' and 'White Cascade' in vigor, internode length, finely dissected leaves, and flower size. 'White Cascade' and 'Avalanche' grow 10–16 cm. in a season. 'White Abundance' is less vigorous, growing 8 cm. in season. The internode length of 'White Abundance' is 5.50–8 cm., which is less than the parent plants. 'White Cascade' and 'Avalanche' exhibit internodes that are 10–16 cm. in length. The leaves of 'White Abundance' are fine in texture. 'White Abundance' exhibits flowers that are 3.50–5 cm. in diameter, as compared to 'Avalanche' which exhibits flowers that are 7–8 cm. in diameter, and 'White Cascade' which exhibits flowers that are 5.50–7 cm. in diameter.

The first asexual propagation was accomplished by the inventor in 1997 and carried out in a cultivated area of Hampshire, England. The method of propagation used was semi-ripe nodal stem cuttings. Since that time, under careful observation, the distinguishing characteristics have been determined stable, uniform and true to type in successive generations.

SUMMARY OF THE INVENTION

The following represent the distinguishing characteristics of the new *Clematis* cultivar 'White Abundance'. In combination these traits set 'White Abundance' apart from all other existing varieties of *Clematis* known to the inventor. 'White Abundance' has not been tested under all possible conditions and phenotypic differences may be observed with variations in environmental, climatic, and cultural conditions, however, without any variance in genotype.

1. *Clematis* 'White Abundance' exhibits fine fern-like green foliage.
2. *Clematis* 'White Abundance' exhibits short internodes.
3. *Clematis* 'White Abundance' produces a profusion of fragrant cream-white flowers in spring.
4. *Clematis* 'White Abundance' is an evergreen sub-shrub.
5. *Clematis* 'White Abundance' exhibits male flowers.
6. *Clematis* 'White Abundance' is 0.75–1.25 meters in height and 0.75–1.25 meters in width at maturity.

BRIEF DESCRIPTION OF THE DRAWINGS

The accompanying drawings illustrate the overall appearance of the new cultivar 'White Abundance', showing the colors as true as it is reasonably possible to obtain in colored reproductions of this type. Colors in the drawings may differ from the color values cited in the detailed botanical description, which accurately describe the actual colors of the new variety 'White Abundance'. The plants in the drawings were grown in an unheated greenhouse in Oregon with minimum night temperatures of minus 6° Centigrade. The plants in the drawings were 18-months-old and in one-liter containers at the time.

The drawing on sheet 1 illustrates the entire plant in bloom from a side perspective.

The drawing on sheet 2 is a close-up view of the flowers. All drawings are made using conventional techniques and although foliage colors may appear different from actual colors due to light reflectance, they are as accurate as possible by conventional photography.

BOTANICAL DESCRIPTION OF THE PLANT

The following is a detailed description of the *Clematis* cultivar named 'White Abundance'. Data was collected in Arroyo Grande, Calif. from plants that were grown in an unheated greenhouse with a minimum night temperature of minus 6° Centigrade. The young plants were 9-months-old and in 10 cm. containers while the mature plants were 18-months-old and in one-liter containers at the time. Color determinations are in accordance with The 2001 Royal Horticultural Society Colour Chart except where general color terms of ordinary dictionary significance are used. The growing requirements are similar to the species.

Botanical classification: *Clematis*×*cartmanii* 'White Abundance'.
Species: *cartmanii.*
Common name: Vase vine.
Uses: Sub-shrub.
Parentage: 'White Abundance' is a hybrid resulting from the induced hybridization of the following parent plants:
*Seed parent.*—*Clematis* 'White Cascade'.
*Pollen parent.*—*Clematis* 'Avalanche'.
Type: Perennial.
Vigor: Moderate vigor.
Habit: Compact.
Height (at maturity): 0.75 to 1.25 meters in height.
Width (at maturity): 0.75 to 1.25 meters in width.
Height (one-liter container): 13 cm. in height from soil level.
Width (one-liter container): 15 cm. in width.
Depth (one-liter container): 17 cm. cascading below edge of container.
Hardiness: Hardy to minus 10° Centigrade.
Propagation: Semi-ripe nodal stem cuttings.
Root system: Fibrous.
Soil: Any well-drained soil.
Sunlight: Good light intensity.
Plant sexuality: Male.
Time to initiate rooting: 6–8 weeks are needed to produce roots on an initial cutting.
Temperature to initiate rooting: 15° to 21° Centigrade air temperature.
Crop time: 12 to 15 months are needed to produce a finished one-liter container from a rooted cutting.
Seasonal interest: Cream-white flowers in spring.
Stem:
*Stem diameter.*—3 mm. in diameter.
*Stem length.*—15 cm. in length.
*Shape.*—Cylindrical.
*Surface.*—Mostly glabrous but with a few minute hairs.
*Stem color.*—N187A.
*Internode length* (*1-liter container*).—5.50–8 cm. between nodes.
*Internode length* (*10 cm. diameter*).—1–3 cm. between nodes.
Foliage:
*Type.*—Evergreen.
*Leaf arrangement.*—Opposite.
*Leaf division.*—Ternate.
*Leaf shape.*—Trifoliage and finely dissected.
*Leaf base.*—Aequilateral.
*Leaf apex.*—Acute at tips of lobes.
*Leaf venation.*—Pinnate with prominent mid-vein.
*Vein color* (*abaxial and adaxial surfaces*).—147A.
*Leaf surface* (*adaxial*).—Glabrous and shiny.
*Leaf surface* (*abaxial*).—Glabrous and matte.
*Leaf pubescence.*—Absent.
*Leaf texture.*—Leathery.
*Leaf attachment.*—Petiolate.
*Petiole dimensions.*—1.50 cm. in length and 1.5 mm. in length.
*Petiole shape.*—Sulcate.
*Petiole color.*—N187A.
*Petiole surface.*—Pubescent.
*Leaf margin.*—Lobed with each lobe margin entire.
*Young leaf dimensions* (*in 10 cm. container*).—1.50 cm. in length and 1.25 cm.in width.
*Young leaf color* (*adaxial and abaxial surfaces*).—139B.
*Mature leaf dimensions.*—2.50 cm. in length and 2.25 cm. in width.
*Mature leaf color* (*adaxial and abaxial surfaces*).—A combination of 147A and N187B.
*Foliar fragrance.*—Absent.
Flower:
*Inflorescence.*—Panicle.
*Flower form.*—Solitary.
*Color of peduncle.*—144A.
*Peduncle length.*—6 cm. in length.
*Peduncle diameter.*—2 mm. in diameter.
*Self-cleaning or persistent.*—Self-cleaning.
*Sexuality.*—Male.
*Dimensions of flower.*—2 cm. in height and 3.50–5 cm. in diameter.
*Flower shape.*—Rotate.
*Aspect.*—Facing outward.
*Petals.*—Apetalous.
*Tepals.*—Six to eight in number.
*Color of tepals* (*abaxial and adaxial surfaces*).—A combination of 155B and 145B.
*Tepal shape.*—Obovate.
*Tepal surface* (*adaxial surface*).—Glabrous and involute midway to apex.
*Tepal surface* (*abaxial surface*).—Pubescent.
*Tepal margin.*—Entire.
*Tepal apex.*—Rounded.
*Tepal base.*—Cuneate.
*Tepal length.*—3 cm. in length.
*Tepal width.*—1.25 cm. in width.
*Unfused or fused.*—Tepals are unfused.
*Peduncle form.*—Tortuous.
*Peduncle color.*—N187A.
*Subtending bracts.*—Four in number.
*Dimensions of subtending bracts.*—6 mm. in length and 3 mm. in width.
*Color of subtending bracts.*—139B.
*Blooming period.*—March to April.
*Bud color.*—144D.
*Bud shape.*—Oval.
*Bud dimensions.*—1.25 cm. in length and 0.75 cm. in width.
*Quantity of flowers.*—Approximately 26–30 per inflorescence.
*Fragrance.*—Perfume scent.
Reproduction organs:
*Stamens.*—Polyandrous.
*Stamen shape.*—Flattened filaments.
*Color of stamens.*—N144C.
*Dimensions of stamen.*—12 mm. in length and 1.5 mm in diameter.
*Dimensions of anther.*—1 mm. in width and 2 mm. in length.
*Pollen color.*—181D.

*Amount of pollen.*—Low.

*Anther color.*—166A.

*Anther shape.*—Basafixed and flattened.

*Ovary.*—Absent.

Seed: 'White Abundance' does not produce seed.

I claim:

1. A new and distinct variety of *Clematis* plant named 'White Abundance' as described and illustrated.

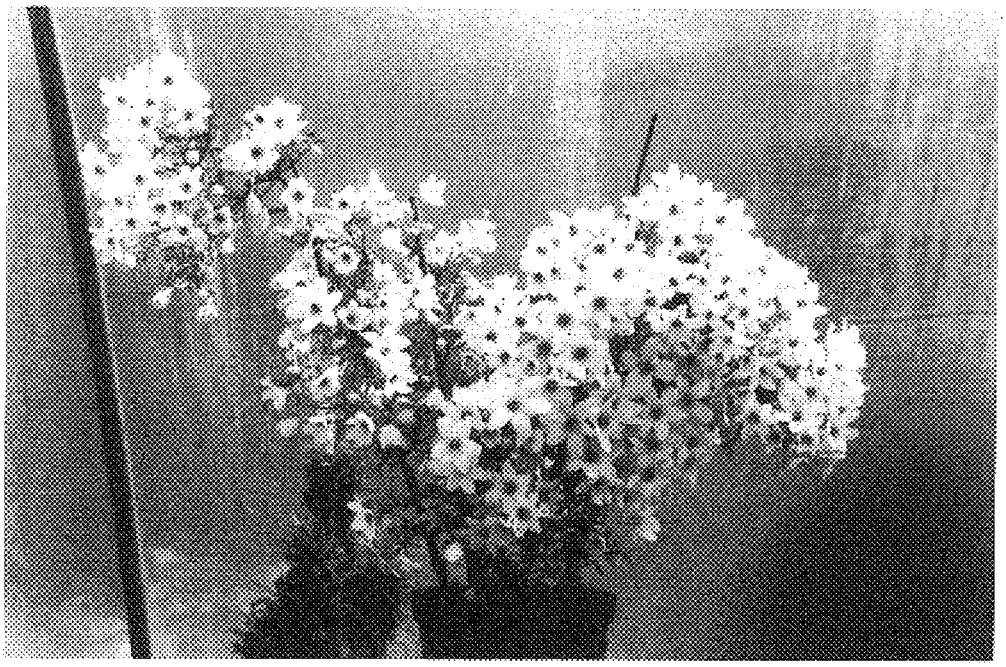

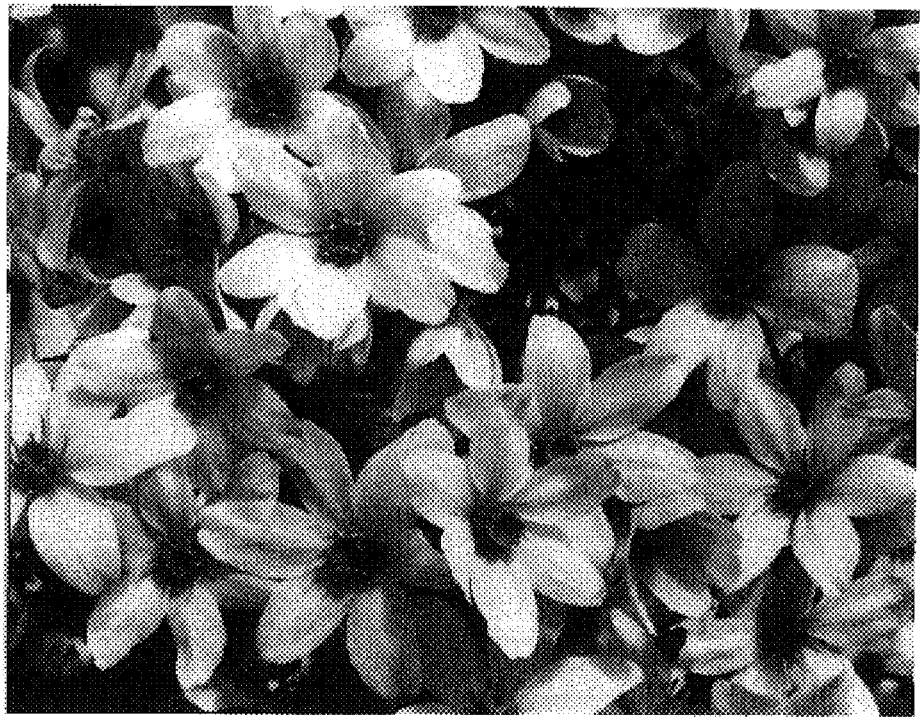

* * * * *